United States Patent
Ober, Jr.

(10) Patent No.: US 11,282,611 B2
(45) Date of Patent: Mar. 22, 2022

(54) CLASSIFYING MEDICAL RECORDS FOR IDENTIFICATION OF CLINICAL CONCEPTS

(71) Applicant: 3M INNOVATIVE PROPERTIES COMPANY, St. Paul, MN (US)

(72) Inventor: Norman S Ober, Jr., Southboro, MA (US)

(73) Assignee: 3M Innovative Properties Company, St. Paul, MN (US)

( * ) Notice: Subject to any disclaimer, the term of this patent is extended or adjusted under 35 U.S.C. 154(b) by 678 days.

(21) Appl. No.: 14/771,895

(22) PCT Filed: Feb. 18, 2014

(86) PCT No.: PCT/US2014/016851
§ 371 (c)(1),
(2) Date: Sep. 1, 2015

(87) PCT Pub. No.: WO2014/133825
PCT Pub. Date: Sep. 4, 2014

(65) Prior Publication Data
US 2016/0019365 A1    Jan. 21, 2016

Related U.S. Application Data

(60) Provisional application No. 61/771,555, filed on Mar. 1, 2013.

(51) Int. Cl.
| | |
|---|---|
| G16H 50/70 | (2018.01) |
| G16H 10/60 | (2018.01) |
| G16Z 99/00 | (2019.01) |
| G06F 40/211 | (2020.01) |

(52) U.S. Cl.
CPC ........... *G16H 50/70* (2018.01); *G06F 40/211* (2020.01); *G16H 10/60* (2018.01); *G16Z 99/00* (2019.02)

(58) Field of Classification Search
CPC ....... G06F 19/34; G06F 17/271; G16H 10/60; G16H 50/70; G06Q 10/10
(Continued)

(56) References Cited

U.S. PATENT DOCUMENTS 5,664,109 A * 9/1997 Johnson ................. G06Q 40/08
705/2
6,292,771 B1    9/2001 Haug
(Continued)

FOREIGN PATENT DOCUMENTS

| WO | WO 2012-122122 | 9/2012 | |
|---|---|---|---|
| WO | WO-2012122122 A1 * | 9/2012 | ......... G06F 16/3344 |
| WO | WO 2014-134026 | 9/2014 | |

OTHER PUBLICATIONS

Deepal Dhariwal,Text and Ontology Driven Clinical Decision Support System, 2013, Published by ProQuest LLC (2013). (Year: 2013).*

(Continued)

*Primary Examiner* — Hiep V Nguyen

(57) ABSTRACT

This disclosure includes a method of classifying a plurality of subjects associated with medical documents. The method includes receiving, with a computer system, an indication of at least one clinical concept, parsing, with the computer system, the medical documents for corresponding indications of the clinical concept, identifying, with the computer system, subjects in the plurality of subjects as meeting the clinical criterion based on prioritization of sections within the medical documents and locations of the corresponding indications of the clinical concept within the medical documents, and outputting, with the computer system, indications of the subjects in the plurality of subjects identified as meeting the clinical criterion.

25 Claims, 15 Drawing Sheets

(58) Field of Classification Search
USPC .............................................................. 705/2
See application file for complete search history.

(56) References Cited

U.S. PATENT DOCUMENTS

| | | | |
|---|---|---|---|
| 6,556,964 B2 | 4/2003 | Haug | |
| 7,720,783 B2 | 5/2010 | Staddon | |
| 7,761,440 B2 | 7/2010 | Chow | |
| 2002/0082825 A1 | 6/2002 | Rowlandson | |
| 2005/0204310 A1 | 9/2005 | De Zwart | |
| 2006/0020465 A1 | 1/2006 | Cousineau | |
| 2007/0143245 A1 | 6/2007 | Dettinger | |
| 2008/0133275 A1 | 6/2008 | Haug | |
| 2008/0288286 A1 | 11/2008 | Noreen | |
| 2009/0070103 A1 | 3/2009 | Beggelman | |
| 2010/0161316 A1 | 6/2010 | Haug | |
| 2012/0110016 A1* | 5/2012 | Phillips | G06Q 10/06 707/780 |
| 2013/0212475 A1* | 8/2013 | Lee | G06F 17/276 715/261 |
| 2014/0181128 A1* | 6/2014 | Riskin | G06Q 10/10 707/756 |
| 2014/0365210 A1* | 12/2014 | Riskin | G06F 17/2765 704/9 |

OTHER PUBLICATIONS

International Search report for PCT International application No. PCT/US2014/16851 dated May 20, 2014, 2 pages.

* cited by examiner

| Hidden Diagnosis | Quantifier (Proxy) | Expert Value | User Value | System Value |
|---|---|---|---|---|
| Hypertension | Blood Pressure (BP) | >140/90 | >130/85 | >150/100 |
| Chronic Renal Failure | Glomerular Filtration Rate (GFR) | <15 | <20 | <17 |
| Alcoholism (EtOH) | Drinks Consumed / Day | >6 | | |
| Substance Abuse | Illicit Drug Use / Day | >2 | >3 | >1 |

CLASSIFYING MEDICAL RECORDS FOR IDENTIFICATION OF CLINICAL CONCEPTS

CROSS REFERENCE TO RELATED APPLICATIONS

This application is a national stage filing under 35 U.S.C. 371 of PCT/US2014/016851, filed Feb. 18, 2014, which claims priority to U.S. Application No. 61/771,555 filed Mar. 1, 2013, the disclosure of which is incorporated by reference in its entirety herein.

TECHNICAL FIELD

This disclosure relates to computer-based analysis of medical records.

BACKGROUND

In the medical field, computer-based storage of medical documentation has become common. In some instances, it may be useful to analyze a multitude of medical documents simultaneously with a computer. As one example, computer-based analysis of a multitude of medical documents can be used to identify patients meeting selected clinical concept criterion, such as criterion for being subjects in a medical study. Because medical documents can include varying data formats, inconsistent terminology and/or varying levels information, accurately classifying which subjects of those associated with the multitude of medical documents meeting selected criterion can be difficult.

SUMMARY

This disclosure is directed to computer-based techniques for searching and identifying clinical concepts within medical documents. In one example, the techniques include finding subjects associated with medical documents including an indication of a selected clinical concept as well as subjects associated with medical documents including indications that correlate to the indication of the selected clinical concept. The indications that correlate to the indication of the selected clinical concept may include ontologies of the indication of the clinical concept. The indications that correlate to the indication of the selected clinical concept may also include quantitative indications of the clinical concept. In another example, the disclosed techniques may include user interfaces suitable for searching and identifying key clinical concepts within medical documentation as well as additional techniques for identifying clinical concepts within medical documents.

In one example, this disclosure is directed to a method of classifying a plurality of subjects associated with medical documents, the method including receiving, with a computer system, an indication of at least one clinical concept, parsing, with the computer system, the medical documents for corresponding indications of the clinical concept, identifying, with the computer system, subjects in the plurality of subjects as meeting the clinical criterion based on subjects who are associated with medical documents that include the indication of the clinical concept, and further based on subjects in the plurality of subjects who are associated with medical documents that include indications that correlate to the indication of the clinical concept received by the computer system, and outputting, with the computer system, indications of the subjects in the plurality of subjects identified as meeting the clinical criterion.

In another example, this disclosure is directed to a computer system-readable storage medium that stores computer system-executable instructions that, when executed, configure a computer system to perform the preceding method.

In another example, this disclosure is directed to a computer system comprising one or more processors configured to perform the preceding method.

In another example, this disclosure is directed to a user interface for a computer system, the user interface being configured to present clinical concept categories as selectable buttons, in response to a user selection of any of the selectable buttons, present a list of clinical concepts within the selected clinical concept category to a user, receive a user indication of a desired attribute of subjects according to one or more of the listed clinical concepts, and in response to the user indication of the desired attribute of subjects, automatically preset, to the user, an indication of a quantity of subjects meeting the desired attribute within a database.

In another example, this disclosure is directed to a method of classifying a plurality of subjects associated with medical documents, the method comprising receiving, with a computer system, an indication of at least one clinical concept; parsing, with the computer system, the medical documents for corresponding indications of the clinical concept; identifying, with the computer system, subjects in the plurality of subjects as meeting the clinical criterion based on prioritization of sections within the medical documents and locations of the corresponding indications of the clinical concept within the medical documents; and outputting, with the computer system, indications of the subjects in the plurality of subjects identified as meeting the clinical criterion.

In another example, this disclosure is directed to a computer system-readable storage medium that stores computer system-executable instructions that, when executed, configure a computer system to perform the preceding method.

In another example, this disclosure is directed to a computer system comprising one or more processors configured to perform the preceding method.

The details of one or more examples of this disclosure are set forth in the accompanying drawings and the description below. Other features, objects, and advantages associated with the examples may be apparent from the description and drawings, and from the claims.

BRIEF DESCRIPTION OF DRAWINGS

FIGS. 8-16 illustrate screenshots of an example user interface for searching and identifying clinical concepts within medical documents.

DETAILED DESCRIPTION

This disclosure is directed to computer-based techniques for searching and identifying key clinical concepts within medical documents. In one example, the techniques include using natural language processing (NLP) for searching and identify key clinical concepts within medical documents. NLP techniques may allow users to analyze data and attain knowledge from electronic medical records and any other available documents that contain either a free text (i.e., unstructured) components and/or structured components. The techniques may include automatic prioritization of where to search based upon clinically sophisticated prioritization and statistically driven logic. System logic may determine or compute a "clinical equivalent" of many key medical definitions even if relevant keywords are not noted in the text of any particular medical document. A computer system may identify potential correlations or hidden inferences within medical documentation to discover vague, potentially misinterpreted, or inaccurate data among structured or unstructured dictated text. In this manner, this disclosure includes computer-based techniques for finding ontologies and quantitative indications of clinical concepts. The disclosed techniques further include classifying subjects associated with medical documents according to selected clinical concepts.

In some examples, the disclosed techniques may be used to identify and screen subjects a population by developing patient profiles based on various diseases and medical history for enrollment in a care management program or enrollment in a clinical trial or research study. In other examples, the techniques disclosed herein may be used to identify potential subjects for drug trials, medical device trials, drug surveillance to quickly measure untoward effects of new medications and disease surveillance to monitor population outbreaks of disease.

Many organizations find it difficult and expensive to develop patient rosters from medical claims data. The accuracy of the selection criteria is often poor due to the lack of clinical data. In addition, patient recruitment can be a significant cost of a clinical trial. With access to large amounts of clinical data, a computer system may find subjects of interest using the techniques disclosed herein.

In this manner, the disclosed techniques may provide one or more of the following advantages: accurate implementation of roster generation, save time on patient identification, save cost on roster, improved study acceptance rates, decrease cost of patient identification/recruitment, and/or increase revenue from participating is clinical trials.

Figure 1:
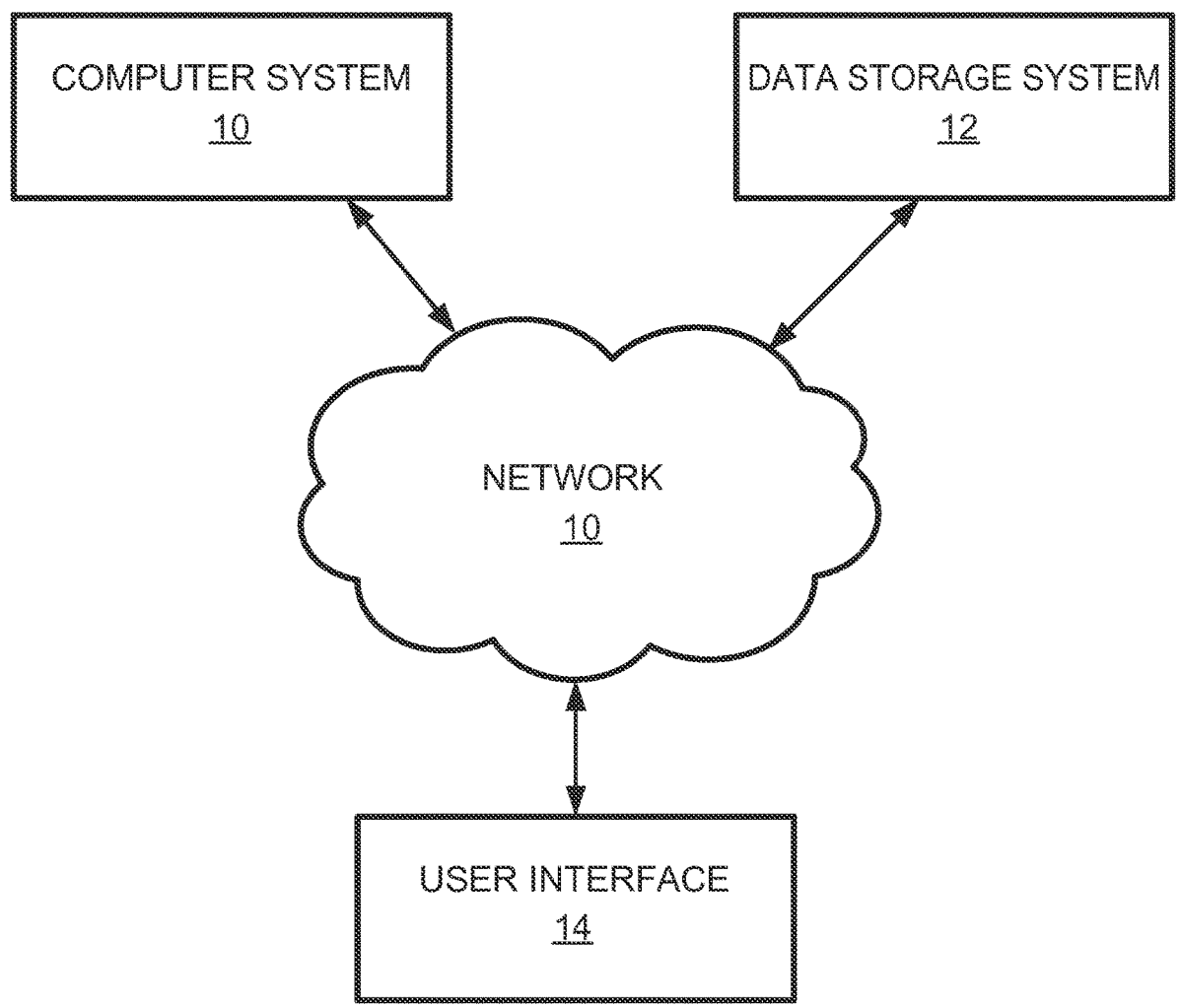
FIG. 1 illustrates a network including computer system for searching and identifying clinical concepts within medical documents.

FIG. 1 illustrates a network including computer system for searching and identifying clinical concepts within medical documents. The network shown in FIG. 1 includes computer system 10, data storage system 12, user interface 14 and network 16, which serves to communicatively couple each of computer system 10, data storage system 12 and user interface 14 to one another. In different examples network 16 may represent a computer bus, a local area network (LAN), a virtual private network (VPN), the Internet, a combination thereof or any other network. For example, network 16 may comprise a proprietary on non-proprietary network for packet-based communication. In one example, network 16 comprises the Internet and data may be transferred via network 16 according to the transmission control protocol/ internet protocol (TCP/IP) standard, or the like. More generally, however, network 16 may comprise any type of communication network, and may support wired communication, wireless communication, fiber optic communication, satellite communication, or any type of techniques for transferring data between a source (e.g., data storage system 12) and a destination (e.g., computer system 10).

In accordance with the techniques described herein, computer system 10, may optionally receive an indication of at least one clinical concept via user interface 14 and output indications of the subjects identified as meeting the clinical concept within a plurality of medical documents. In some examples, computer system 10 may access data storage system 10 to retrieve all or a portion of the medical documents, to retrieve predetermined ontologies and/or quantitative factors associated with the clinical concept and/or store the indications of the subjects identified as meeting the clinical concept within a plurality of medical documents.

As referred to herein, an indication of a clinical concept may be a label for the clinical concept, such as a word, phrase, acronym, abbreviation, or other label for the clinical concept. As discussed below, an indication of a clinical concept that corresponds to a selected indication of a clinical concept may be considered analogous to the selected indication of the clinical concept. In different examples, an indication of a clinical concept that corresponds to a selected indication of a clinical concept may represent an ontology of the selected indication of the clinical concept or quantitative factors associated with the clinical concept.

Figure 2:
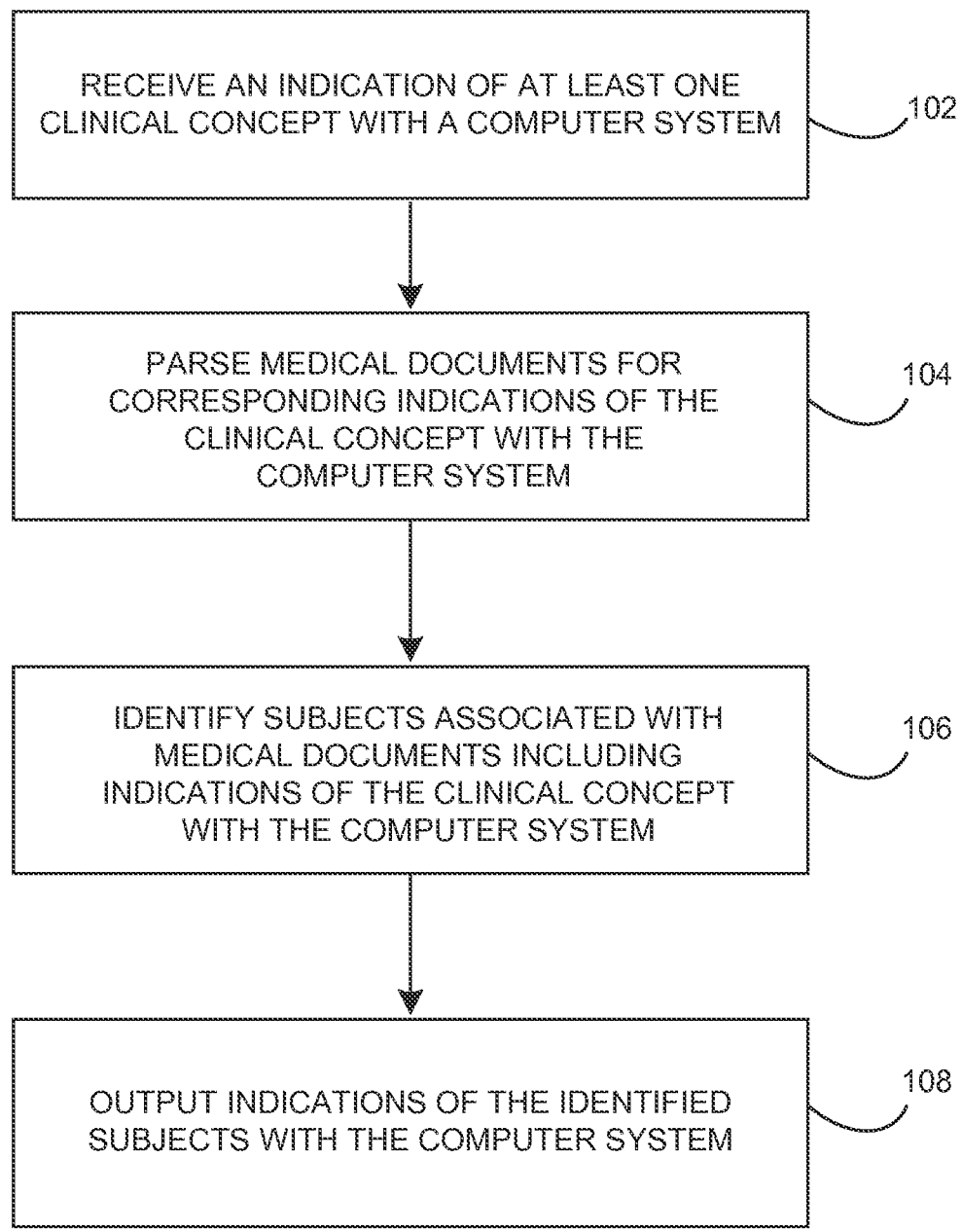
FIG. 2 is a flowchart illustrating example techniques for searching and identifying clinical concepts within medical documents.

FIG. 2 is a flowchart illustrating example techniques for searching and identifying clinical concepts within medical documents. As shown in FIG. 2, the techniques include receiving, with a computer system, such as computer system 10 (FIG. 1) an indication of at least one clinical concept (102). As referred to herein a clinical concept may represent any attribute of subject, such as a patient, associated with a medical document. Such attributes include, but are not limited to, a chief complaint of the subject, a history of present illness of the subject, a past medical history of the subject, a social history of the subject, a family history of the subject, a review of systems of the subject, allergies of the subject, medications of the subject, impressions of the subject by a clinician, a medical plan for the subject, diagnostic imaging results preformed the subject, results of a medical test of the subject, a gender of the subject, an ethnicity of the subject, an age of the subject, a physical attribute of the subject, physical signs of the subject, physical systems of the subject, a time period associated with one of the preceding attributes or another attribute, and/or other attributes. A clinical concept may be associated with subjects associated with a selected attribute, not associated with a selected attribute, and/or associated with subjects for which the selected attribute is unknown. The indication of the clinical concept may optionally include an indication of whether the clinical concept is associated with subjects associated with a selected attribute, not associated with a selected attribute, and/or associated with subjects for which the selected attribute is unknown.

After receiving the indication of at least one clinical concept, the computer system parses medical documents for corresponding indications of the clinical concept (104). Optionally, the computer system may index data parsed from the medical documents to facilitate parsing for corresponding indications of the clinical concept. In addition, the computer system may retrieve the medical documents from memory or from a data storage system, such as data storage system 12 (FIG. 1). Optionally, the computer system may acquire the medical documents by receiving the medical documents and/or an indication of location(s) of the medical documents via a network connection.

In some examples, the medical documents may include any of the following categories medical documents: government-acquired medical documents from a Medicare repository, medical documents submitted to a government by the medical facility, medical documents submitted to the government by many medical facilities, medical documents received from one or more medical facilities, medical documents received from one or more insurance companies, medical documents associated with all-payer health insurance claims, and other medical documents. As referred to herein medical facilities include hospitals, clinics, laboratories performing analysis or medical testing and other facilities associated with the treatment or diagnosis of medical patients.

In the same or different examples, the medical documents may include medical clinician notes, medical clinician dictations, medication files, radiology reports, emergency department, subject pathology reports, and other medical documents. In more specific examples, the medical documents may include documents associated with one or more of the following: allied services—occupational therapy, allied services—physical therapy, emergency department—nursing, emergency department—physician, emergency department—triage, inpatient—admission nursing note, inpatient—admission physician history and physical, inpatient—discharge instructions, inpatient—discharge summary, inpatient—nursing progress, inpatient—physician discharge summary, inpatient—physician orders, inpatient—physician progress, medical specialty—cardiology, medical specialty—endocrinology, medical specialty—gastroenterology, medical specialty—pulmonology, medical specialty—radiology, operative procedures, outpatient—nursing progress notes, outpatient—physician progress notes, pathology—anatomic, pathology—laboratory, surgery specialty—cardiac surgery, surgery specialty—obstetrics and gynecology, surgery specialty—orthopedic surgery and other documents. The medical documents listed and described herein are merely examples. The techniques described herein may be applied to any type of medical documents including attributes of subjects, such as patients.

The computer system then identifies subjects, such as patients, as meeting the clinical criterion based on subjects who are associated with medical documents that include the indication of the clinical concept (106). The computer system outputs the indications of the identified subjects (108). For example, the computer system may store the indications of the identified subjects on a data storage system and/or the computer system may present the indications of the identified subjects to a user. In some examples, the computer system may send the indications of the identified subjects to a client computer via a network, such as network 16 (FIG. 1) using an IP or other protocol. The client computer may then present the indications of the identified subjects to a user; e.g., via a user interface, such as user interface 14 (FIG. 1).

Figure 3:
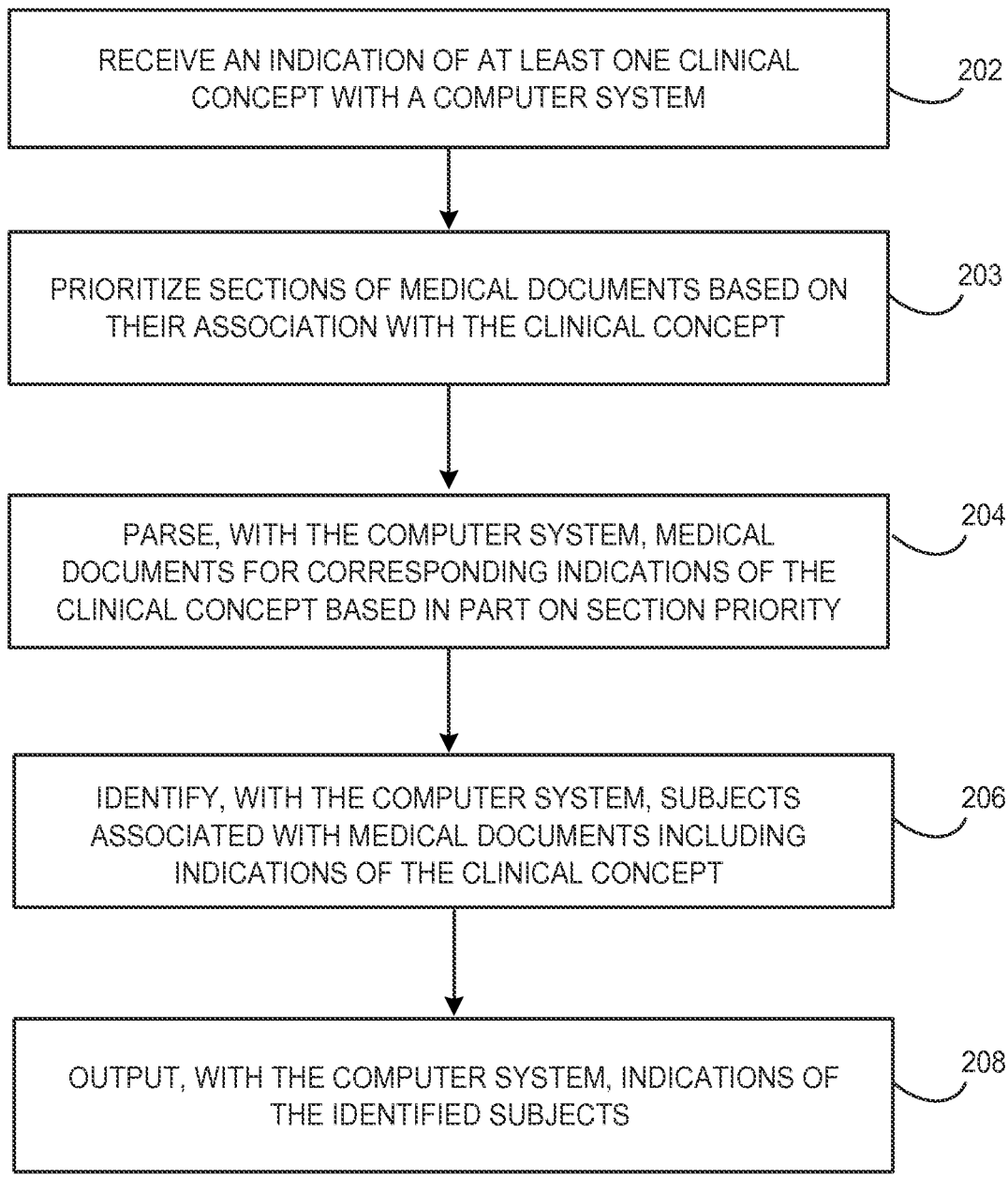
FIG. 3 is a flowchart illustrating example techniques for searching and identifying clinical concepts within medical documents based on prioritizing sections of the medical documents.

FIG. 3 is a flowchart illustrating example techniques for searching and identifying clinical concepts within medical documents based on prioritizing sections of the medical documents. The techniques disclosed in FIG. 3 generally include the techniques of FIG. 2 with the addition of prioritizing sections of the medical documents in order to facilitate identification of subjects associated with indicated clinical concepts. For brevity, details of the techniques illustrated FIG. 3 that are the same or similar to the techniques illustrated FIG. 2 are described in limited or no detail with respect to FIG. 3.

As shown in FIG. 3, the techniques include receiving, with a computer system, such as computer system 10 (FIG. 1) an indication of at least one clinical concept (202). After receiving the indication of at least one clinical concept, the computer system prioritizes sections of medical documents based on associations of the sections to the clinical concept (203).

The computer system may prioritize sections of medical documents using intelligent document section specific query logic. For example, in creating medical records, physicians (and other types of clinicians) tend to utilize a standardized approach for annotating a patient encounter.

While there are numerous types of documents dictated, there are four general types of encounter documents that most physicians are trained to develop.

One such encounter document is standardized history and physical (H&P). This format is used during a comprehensive patient evaluation. Please note that the exact sections may vary by institution and not all sections may be available during each encounter. The sections may also vary by clinical specialty. The order of "sections" may also vary. This is the standard format used by electronic medical record (EMR) companies. The H&P format in general is as follows:

Chief complaint (CC)
History of present illness (HPI)
Past medical history (PMH)
Social history (SH)
Family history (FH)
Review of systems (ROS)
Allergies
Medications (RX)
Impression (IMP)
Plan Each of the above sections contains information relevant to that particular section. For example, "family history" may contain information on major diseases suffered by a patient's parents, siblings and children. Social history always contains information on a patient's use of alcohol, illicit drugs, tobacco use, occupation, and living situation. ROS is a very extensive list of physical exam detailed findings from a patient's head to toe (literally).

Another such encounter document is a SOAP note. SOAP is an acronym for:

Subjective—A review of a patient's symptoms (E.g., pain level, complaints, etc.)

Objective—Results of any exam (E.g., EKG, lung exam findings, etc.)

Assessment—What the clinician thinks about the patient's situation (E.g., "I think the patient still has a small bowel obstruction")

Plan—What the clinician is planning to do for the patient at this point in time (E.g., "We may leave the patient's GI tube in place for the next 24 hours and evaluate its output with potential removal in the morning").

Another such encounter document is a Procedure/operative note: This represents a very free form note where clinicians dictate/write their encounter with a patient after performing a certain procedure. For example, the note for the placement of a "central line" could read as simple as "The patient's right external jugular vein was prepped and draped in the standard fashion following all sterile protocols. A number 12 needle and catheter was inserted after the administration of 2 ccs of lidocaine in the area . . . etc." An operative report would be much more extensive and would describe a major surgical procedure in detail, such as a total hip replacement. This type of note might read like "The patient entered the OR in stable condition . . . After the induction of general anesthesia a 20 cm incision was made in the left lateral femoral area exposing the proximal femur . . . ."

Another such encounter document is an update/progress note: This represents a very free form note where clinicians dictate/write very quick updates to a patient's condition and/or update to their test results. During a hospital visit, it could state something as simple as "Patient is fine today." However, the note could be much more detailed and state the results of a major procedure such as "The patient's cardiac catherization showed occlusion in all 5 major vessels with each vessel being stenotic over 80% . . . " There is often no heading identifying these of sections in medical records. However, many institutions call these progress notes.

The computer system may search for key clinical concepts using NLP and automatically prioritize the sections on where to search based upon clinically sophisticated prioritization logic. While clinicians tend to utilize a standardized approach for annotating a patient encounter, how the document is dictated, including how the sections are labeled, the order of the sections, whether or not section titles exist and, if so, whether the sections are explicitly marked, varies tremendously between different institutions and between doctors at the same institution. Indeed, an individual doctor's dictation patterns may vary, either based upon the type of exam or procedure they are performing, or for completely arbitrary reasons. An NLP engine may perform a regioning analysis on each document, to map the variation to the standard note types and normalized region titles listed above. This analysis informs the search filtering and boosting criteria outlined above.

In one example, a user may want to evaluate all cases of patients who present to their physician with the symptom of "cough." The computer system may search only in the "chief complaint" field for this clinical concept, even though the keyword "cough" may appear in many other areas of a numerous notes associated with a subject.

In another example, a user may want to evaluate all cases of patients who present to their physician with high blood pressure (hypertension). The user does not care if the patient has presented to a particular hospital department or not, they just want to know that the patient has this chronic condition. For this analysis, the computer system may know to look for the key words associated with high blood pressure (using clinically sophisticated/intelligent ontologies, see below) in the appropriate sections of all the medical record documents. For example, this condition may appear in the following fields: chief complaint, history of present illness, past medical history, and/or impression. A key feature of NLP capability is the diagnosis of hypertension may occur without appearing as a code, such as an ICD9 code, in the medical document.

As another example, in searching for a clinical concept, the computer system may prioritize where to search for the concept based on the type of concept requested. This may improve the accuracy of concept identification from the system. This is extremely important when there is conflicting data in the same record for the same patient. For example, if a user is seeking patients who smoke, the system may return the concept that the patient is a smoker from the HPI section of the note and that the patient is not a smoker from the SH section of the note. In addition to flagging this inconsistency, the computer system may select the most clinically likely scenario. For example, if the patient were being evaluated for chest pain, the most accurate scenario for smoking information would be in the HPI field. However, if the patient is being evaluated for a broken ankle, the SH field would be the more likely appropriate section where smoking history would be defined. The rationale is based on the clinical likelihood of smoking being related to the main condition for which the patient is being evaluated.

While most clinical institutions have a standardized form of how to dictate free text documents, there are many variances. The NLP engine may direct the user to the appropriate section based on whether the "key word" or "clinical concept" is a diagnosis, sign, symptom, etc. Some of these analyses may involve complicated string searches that may be "pre-coded" and saved in drop down menus, such as those illustrated in FIGS. 8-15.

After prioritizing sections of medical documents based on associations of the sections to the clinical concept, the computer system then parses medical documents for corresponding indications of the clinical concept based on prioritization of sections within the medical documents and locations of the indications of the clinical concept received by the computer system and locations of indications that correlate to the indication of the clinical concept received by the computer system (204).

Optionally, the computer system may index data parsed from the medical documents to facilitate parsing for corresponding indications of the clinical concept. In addition, the computer system may retrieve the medical documents from memory or from a data storage system, such as data storage system 12 (FIG. 1). Optionally, the computer system may acquire the medical documents by receiving the medical documents and/or an indication of location(s) of the medical documents via a network connection.

The computer system then identifies subjects, such as patients, as meeting the clinical criterion based on subjects who are associated with medical documents that include the indication of the clinical concept and further based on prioritization of sections within the medical documents and locations of the indications of the clinical concept received by the computer system and locations of indications that correlate to the indication of the clinical concept received by the computer system (206).

The computer system then outputs the indications of the identified subjects (208). For example, the computer system may store the indications of the identified subjects on a data storage system and/or the computer system may present the indications of the identified subjects to a user. In some examples, the computer system may send the indications of the identified subjects to a client computer via a network, such as network 16 (FIG. 1) using an IP or other protocol. The client computer may then present the indications of the identified subjects to a user; e.g., via a user interface, such as user interface 14 (FIG. 1).

Figure 4:
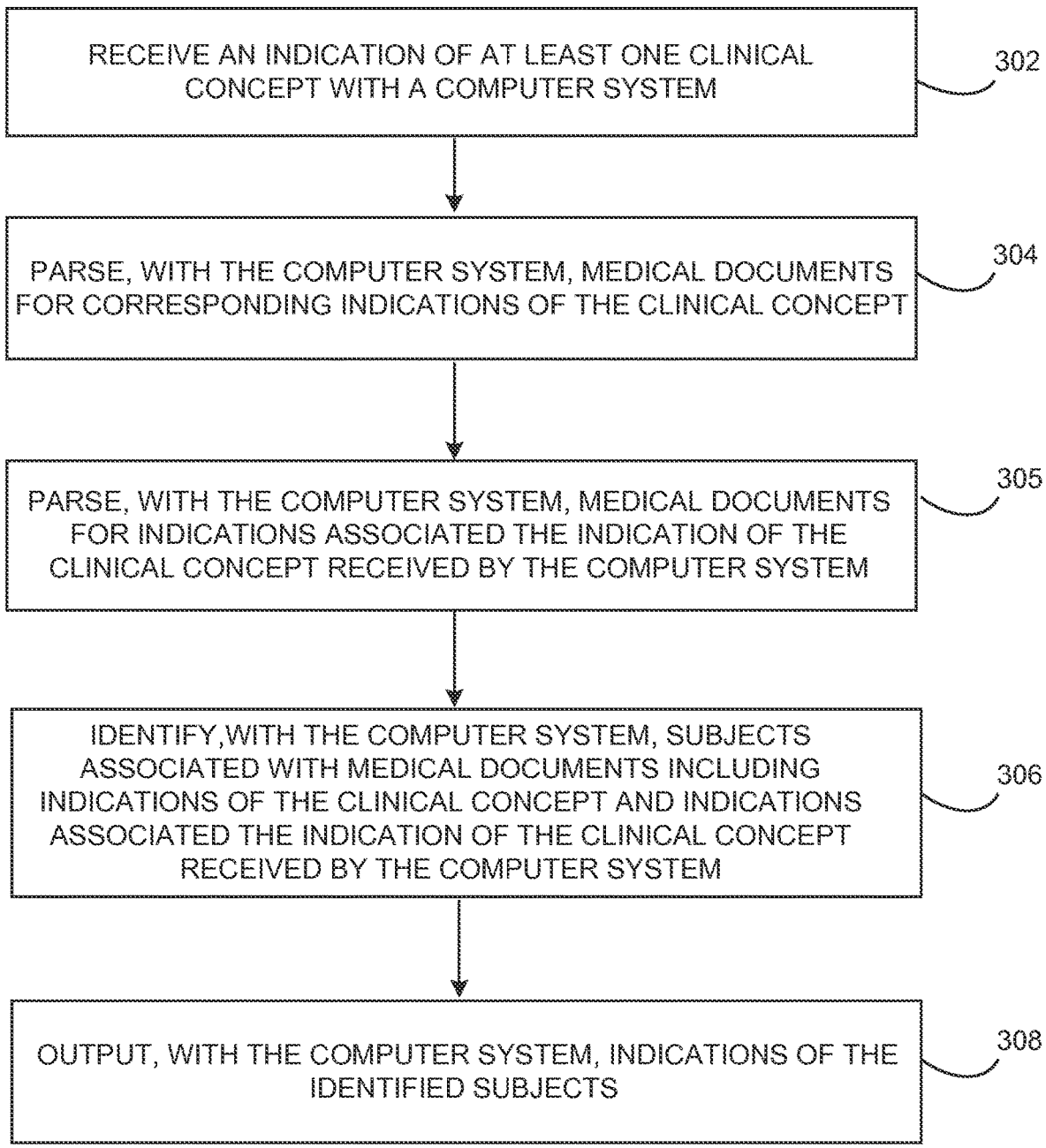
FIG. 4 is a flowchart illustrating example techniques for searching and identifying clinical concepts within medical documents based on indications that correlate to an indication of a selected clinical concept.

FIG. 4 is a flowchart illustrating example techniques for searching and identifying clinical concepts within medical documents based on indications that correlate to an indication of a selected clinical concept. The techniques disclosed in FIG. 4 generally include the techniques of FIG. 2 with the addition of associating indications that correlate to an indication of a selected clinical concept with the clinical concept. In different examples, the associating indications that correlate to an indication of a selected clinical concept may include ontologies of the indication of the clinical concept and/or quantitative indications of the clinical concept. For brevity, details of the techniques illustrated FIG. 4 that are the same or similar to the techniques illustrated FIG. 2 are described in limited or no detail with respect to FIG. 4.

As shown in FIG. 4, the techniques include receiving, with a computer system, such as computer system 10 (FIG. 1) an indication of at least one clinical concept (302). After receiving the indication of at least one clinical concept, the computer system parses medical documents for corresponding indications of the clinical concept (304). The computer system also parses medical documents for indications that correlate to the indication of the clinical concept, such as ontologies of the indication of the clinical concept and/or quantitative indications of the clinical concept (304). Optionally, the computer system may index data parsed from the medical documents to facilitate parsing for corresponding indications of the clinical concept. In addition, the computer system may retrieve the medical documents from memory or from a data storage system, such as data storage system 12 (FIG. 1). Optionally, the computer system may acquire the medical documents by receiving the medical documents and/or an indication of location(s) of the medical documents via a network connection.

The computer system then identifies subjects, such as patients, as meeting the clinical criterion based on subjects who are associated with medical documents that include the indication of the clinical concept and further based on subjects in the plurality of subjects who are associated with medical documents that include indications that correlate to the indication of the clinical concept received by the computer system (306).

As previously mentioned, the indications that correlate to the indication of the clinical concept received by the computer system may include ontologies of the indication of the clinical concept received by the computer system. In other examples, the computer system may identify ontologies of the indication of the clinical concept received by the computer system by analyzing medical documents that include indications of the clinical concept matching the indication of the clinical concept received by the computer system. Such analysis may include, for example, running a natural language (NLP) engine, with the computer system, to search the medical documents that include indications of the clinical concept matching the indication of the clinical concept received by the computer system for textual similarities.

Such analysis may also include statistically analyzing the distribution, incidence and prevalence of terms within the medical documents that include indications of the clinical concept matching the indication of the clinical concept received by the computer system, comparing the distribution, incidence and prevalence of the terms within the medical documents that include indications of the clinical concept matching the indication of the clinical concept received by the computer system with the distribution, incidence and prevalence of the same terms within all the medical documents to find terms correlated with the indications of the clinical concept, and identifying the terms that correlate to the indications of the clinical concept in the medical documents that include indications of the clinical concept matching the indication of the clinical concept received by the computer system as ontologies of the indication of the clinical concept.

In other examples, the indications that correlate to the indication of the clinical concept received by the computer system may include quantitative indications of the clinical concept. For example, if the clinical concept is hypertension, quantitative indications of the clinical concept may include blood pressures above a defined range.

In examples where the indications that correlate to the indication of the clinical concept received by the computer system may include quantitative indications of the clinical concept, the computer system may access a database identifying the quantitative indications of the clinical concept.

In the same or different examples, the computer system may identify the quantitative indications of the clinical concept by analyzing the medical documents that include indications of the clinical concept matching the indication of the clinical concept received by the computer system. Such analysis may include searching medical documents that include indications of the clinical concept matching the indication of the clinical concept received by the computer system for quantitative similarities.

Such analysis may also include statistically analyzing the distribution, incidence and prevalence of quantitative factors within the medical documents that include indications of the clinical concept matching the indication of the clinical concept received by the computer system, comparing the distribution, incidence and prevalence of the quantitative factors within the medical documents that include indications of the clinical concept matching the indication of the clinical concept received by the computer system with the distribution, incidence and prevalence of the same quantitative factors within all the medical documents to find quantitative factors correlated with the indications of the clinical concept, and identifying the quantitative factors that correlate to the indications of the clinical concept as the quantitative indications of the clinical concept.

In some examples, the computer system may access a database or library identifying ontologies of the indication of the clinical concept received by the computer system and or identifying quantitative indications of the clinical concept.

An ontology library may include clinically relevant synonyms. Such clinically relevant synonyms may include synonyms from a Health Data Dictionary (HDD). The clinically relevant synonyms may further include other definitions, words and phrases from various databases, such as databases within the public domain. Available sources of clinically relevant synonyms include definitions from coding systems, such as ICD9, ICD10, CPT4, SNOMED, HCPC and large clinical definition databases such as the Unified Medical Language System (UMLS). Clinically relevant synonyms may also include expert opinions of additional words and phrases.

As an example the following words and phrases may be listed as being clinically relevant synonyms of each other: Type 2 diabetes, prediabetes, glucose intolerance, Adult-Onset diabetes, Maturity-Onset diabetes, noninsulin-dependent diabetes mellitus and ketoacidosis-resistant diabetes.

An ontology library may further include clinical acronyms and physician "short-hand." Clinicians often use acronyms and shorthand phrases when dictating clinical records. While some of these are accepted as "official" abbreviations, many have come into being over the years by frequent use among clinicians. These terms may be included within an ontology library to make the ontology library more robust and reflective of the "real world" of clinical dictation.

As an example, including acronyms and short-hand phrases with the clinically relevant synonyms listed above provides additional ontologies: Type 2 diabetes, IDDM, prediabetes, DMII, DM2, glucose intolerance, T2DM, NIDDM, Adult-Onset diabetes, Maturity-Onset diabetes, MODY, noninsulin-dependent diabetes mellitus, and ketoacidosis-resistant diabetes.

As another example, when looking for subjects associated with the clinical concept of "major depression," the following phrases may also indicate the clinical concept of major depression: suicide attempt, suicidal ideation, and drug overdose. As another example, in seeking subjects associated with the clinical concept of alcoholism, a computer system may find patients having terms and clinical concepts such as "drinks more than 3 bottles of wine each day," "has a six pack of beer each evening." As this example, illustrates the word alcohol does not appear anywhere in medical documents in order for the clinical concept of alcoholism to be identified.

In some examples, the computer system may define ontologies and quantitative indications of the clinical concept according to a user selection. In such examples, ontologies and quantitative indications of the clinical concept may be user-specified and stored in a database. When an indication of a clinical concept, such as a keyword is entered into the computer system, an NLP engine may search the user-specified database for words related to the keyword and search the documentation for the keyword and related words as well as quantitative indications of the clinical concept. For example, in the case of searching for hypertensive patients, a user may want to define hypertension as patients with a blood pressure greater than 150/100.

In further examples, the computer system may define ontologies and quantitative indications of the clinical concept according correlations between known indications of the clinical concept and terms and quantitative factors within medical documents including the known indications of the clinical concept to find "hidden clinical concepts" within other medical documents. The correlations of the hidden clinical concepts may become apparent by comparing the incidence of terms and quantitative factors within medical documents including known indications of the clinical concept as compared to an entire set of medical documents. These found correlations between known indications of the clinical concept and terms and quantitative factors within medical documents may then be used to identify potential hidden clinical concepts within medical document that do not include previously known indications of the clinical concept.

Ontologies and quantitative indications may be defined by a computer system through machine learning normative (or other) statistical assessment. As an example, when an indication of a clinical, such as a keyword, is inserted a computer system, an NLP engine may search documentation for textual and quantitative similarities. As an example, if the keyword is hypertension, medical documents may be be analyzed to determine what statistical blood pressure measurements were recorded with the word hypertension identified using a training data set. The data computed value might be sought in subsequent documents and assigned as a document associated with hypertension even if the keyword or other previously known indication of the clinical condition of hypertension is not specifically mentioned in the document. In essence, hidden or not clearly identified diagnoses in documentation may be inferred through statistical machine computation.

Figures 5, 6:
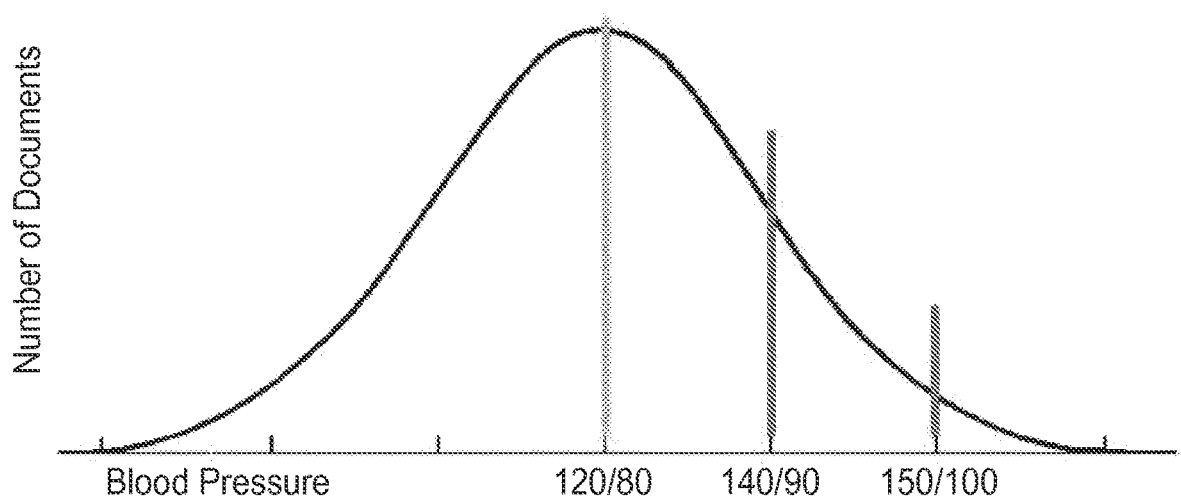
FIG. 5 illustrates an example distribution of blood pressures indications within a plurality medical documents.
FIG. 6 illustrates a table of example quantitative factors associated with example clinical concepts.

FIG. 5 illustrates an example distribution of subject blood pressures recorded within a plurality of medical documents. As shown in FIG. 5, the blood pressures form a bell curve. The center of the bell curve is located at a blood pressure of 120/80. On average, due to the normative nature of the measurement, the majority of documents may contain blood pressure values within one or two standard deviations from the expected value of 120/80. Other parameters can also be modeled as normative distributions permitting repeatable calculations or inferences.

The blood pressures indicated in the distribution may then be compared to blood pressures of medical documents including a known indication of the clinical condition of hypertension. For example, the computer system may find a high probability of documents within one or two deviations of 140/90 or greater than that value contained the keyword "hypertension." Upon computation, the computer system may henceforth infer that values within specified deviations or greater than a value may be designated as hypertension even if the word or ontologies thereof do not appear in the text. For example, medical documents including a known indication of the clinical condition of hypertension would likely provide a much higher distribution of blood pressures, such that the computer system may associate any blood pressure greater than 150/100 with hypertension, even though such an indication of hypertension was not previously known by the computer system.

Referring now to FIG. 6, indications of a clinical concept may be identified accordingly to predetermined associations, an ontology library representing expert opinion, by user-defined data and/or by ontologies and quantitative indications may be defined by a computer system through machine learning normative (or other) statistical assessment. FIG. 6 illustrates lists example clinical conditions along with possible ranges using predetermined associations, and user-defined data and by ontologies and quantitative indications defined by a computer system.

With reference back to FIG. 4, after identifying subjects as meeting the clinical criterion, the computer system then outputs the indications of the identified subjects (308). For example, the computer system may store the indications of the identified subjects on a data storage system and/or the computer system may present the indications of the identified subjects to a user. In some examples, the computer system may send the indications of the identified subjects to a client computer via a network, such as network 16 (FIG. 1) using an IP or other protocol. The client computer may then present the indications of the identified subjects to a user; e.g., via a user interface, such as user interface 14 (FIG. 1).

Figure 7:
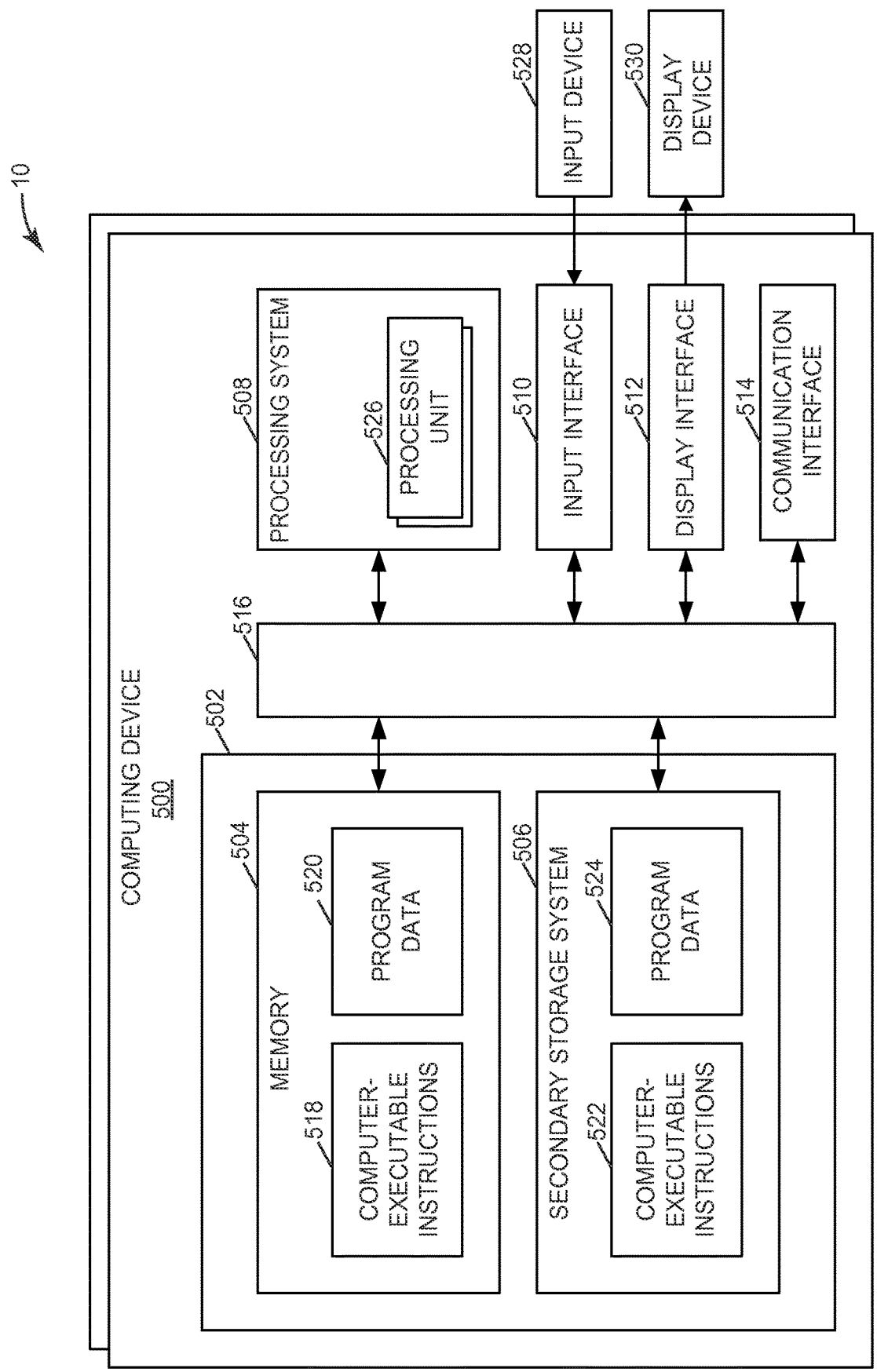
FIG. 7 is a block diagram of an example configuration of a computer system, which may be used to searching and identifying clinical concepts within medical documents and present indications of subjects associated within the identified clinical concepts to a user.
Figure 9:
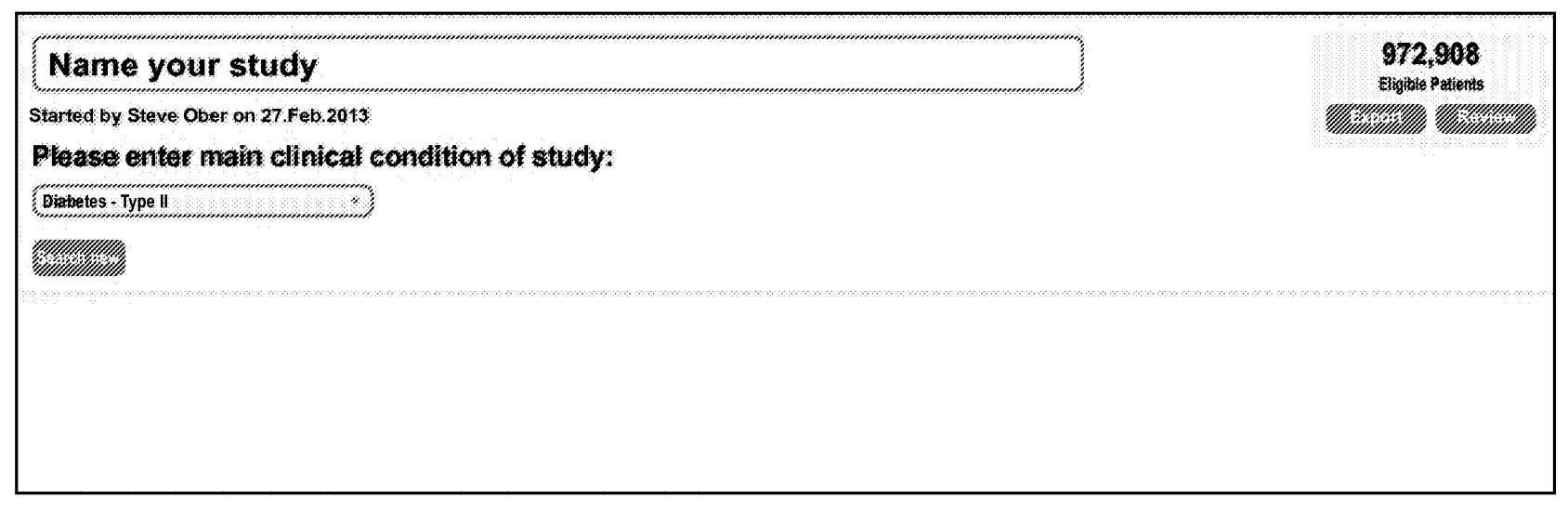

FIG. 7 is a block diagram of an example configuration of a computer system 10, which may be used to preform techniques disclosed herein, including the techniques of FIGS. 2-4. For example, computer system 10 may be used to search and identify clinical concepts within medical documents and present indications of subjects associated within the identified clinical concepts to a user. In the example of FIG. 9, computer system 10 comprises a computing device 500 and one or more other computing devices.

Computing device 500 is a physical device that processes information. In the example of FIG. 7, computing device 500 comprises a data storage system 502, a memory 504, a secondary storage system 506, a processing system 508, an input interface 510, a display interface 512, a communication interface 514, and one or more communication media 516. Communication media 516 enable data communication between processing system 508, input interface 510, display interface 512, communication interface 514, memory 504, and secondary storage system 506. Computing device 500 can include components in addition to those shown in the example of FIG. 7. Furthermore, some computing devices do not include all of the components shown in the example of FIG. 7.

A computer system-readable medium may be a medium from which a processing system can read data. Computer system-readable media may include computer system storage media and communications media. Computer system storage media may include physical devices that store data for subsequent retrieval. Computer system storage media are not transitory. For instance, computer system storage media do not exclusively comprise propagated signals. Computer system storage media may include volatile storage media and non-volatile storage media. Example types of computer system storage media may include random-access memory (RAM) units, read-only memory (ROM) devices, solid state memory devices, optical discs (e.g., compact discs, DVDs, Blu-ray discs, etc.), magnetic disk drives, electrically-erasable programmable read-only memory (EEPROM), programmable read-only memory (PROM), magnetic tape drives, magnetic disks, and other types of devices that store data for subsequent retrieval. Communication media may include media over which one device can communicate data to another device. Example types of communication media may include communication networks, communications cables, wireless communication links, communication buses, and other media over which one device is able to communicate data to another device.

Data storage system 502 may be a system that stores data for subsequent retrieval. In the example of FIG. 7, data storage system 502 comprises memory 504 and secondary storage system 506. Memory 504 and secondary storage system 506 may store data for later retrieval. In the example of FIG. 7, memory 504 stores computer system-executable instructions 518 and program data 520. Secondary storage system 506 stores computer system-executable instructions 522 and program data 524. Physically, memory 504 and secondary storage system 506 may each comprise one or more computer system storage media.

Processing system 508 is coupled to data storage system 502. Processing system 508 may read computer system-executable instructions from data storage system 502 and executes the computer system-executable instructions. Execution of the computer system-executable instructions by processing system 508 may configure and/or cause computing device 500 to perform the actions indicated by the computer system-executable instructions. For example, execution of the computer system-executable instructions by processing system 508 can configure and/or cause computing device 500 to provide Basic Input/Output Systems (BIOS), operating systems, system programs, application programs, or can configure and/or cause computing device 500 to provide other functionality.

Processing system 508 may read the computer system-executable instructions from one or more computer system-readable media. For example, processing system 508 may read and execute computer system-executable instructions 518 and 522 stored on memory 504 and secondary storage system 506.

Processing system 508 may comprise one or more processing units 526. Processing units 526 may comprise physical devices that execute computer system-executable instructions. Processing units 526 may comprise various types of physical devices that execute computer system-executable instructions. For example, one or more of processing units 526 may comprise a microprocessor, a processing core within a microprocessor, a digital signal processor, a graphics-processing unit, or another type of physical device that executes computer system-executable instructions.

Input interface 510 may enable computing device 500 to receive input from an input device 528. Input device 528 may comprise a device that receives input from a user. Input device 528 may comprise various types of devices that receive input from users. For example, input device 528 may comprise a keyboard, a touch screen, a mouse, a microphone, a keypad, a joystick, a brain-computer system interface device, or another type of device that receives input from a user. In some examples, input device 528 is integrated into a housing of computing device 500. In other examples, input device 528 is outside a housing of computing device 500. In some examples, input device 528 may receive one or more indications of clinical concepts from a user and/or other types of data as described above.

Display interface 512 may enable computing device 500 to display output on a display device 530. Display device 530 may be a device that presents output. Example types of display devices include printers, monitors, touch screens, display screens, televisions, and other types of devices that display output. In some examples, display device 530 is integrated into a housing of computing device 500. In other examples, display device 530 is outside a housing of computing device 500. In some examples, display device 530 may present subjects identified as meeting a selected clinical concept or other types of data as described above.

Communication interface 514 may enable computing device 500 to send and receive data over one or more communication media. Communication interface 514 may comprise various types of devices. For example, communication interface 514 may comprise a Network Interface Card (NIC), a wireless network adapter, a Universal Serial Bus (USB) port, or another type of device that enables computing device 500 to send and receive data over one or more communication media. In some examples, communication interface 514 may receive medical documents, indications of clinical concepts, and/or other types of data as described above. Furthermore, in some examples, communication interface 514 may output indications of subjects identified as meeting a selected clinical concept and/or other types of data as described above.

FIGS. 8-15 illustrate screenshots of an example user interface for searching and identifying clinical concepts within medical documents. As an example, the example user interface may be presented on a display of a computer system, such as computer system 10 or on a client computer connected to such a computer system.

As illustrated by FIGS. 8-15, the user interface is designed to follow the logical workflow of a clinical evaluation. The user interface allows a user to select several "filters" for the data they are seeking, such as dates of service range, type of records they want to query, specific clinics they want to query, and temporality of events/diagnoses over the course of time within a given case. Users may also specify filters such as document types on individual search criteria level. As one example, a user may look for drug use in social history or diabetes in a SOAP note.

In one example, a user may use a "top-to-bottom" on their selection criteria according to the following query section:
  Demographics (E.g., select patient gender, age range, etc.)
  Symptoms
  Signs
  Conditions (E.g., search ICD9 and/or text)
  Allergies
  Social History
  Family History
  Surgical/Invasive Procedures (E.g., search CPT4 and/or text)
  Diagnostic Imaging (E.g., search CPT4 and/or text)
  Labs (E.g., search CPT4 and/or text)
  Medications As shown in FIGS. 8-15, the user interface may look similar for each query section.

In different examples, the user interface may allow a user to archives old searches, start new searches, resumes recent searches.

In further examples, the computer system may analyze query submitted in "real time," and the user interface may present an indication of the number of subjects that meet the selected criteria immediately following the analysis of the computer system. This may allow the user to determine exactly where they are in their search process with an appropriate number of patient cases for their study, program enrollment, etc. For example, if a user starts with just looking for patients with diabetes, the number of patients found may immediately appear on the screen. As the user continues to add criteria (inclusion or exclusion), more cases may be eliminated. However, the impact of adding a search criteria is immediately available to the user. This is crucial as it saves time and resources by offering the possibility to change criteria on the fly. For example, assume a user starts with a data set of 1,000 patients with diabetes. He/she wants to find only females. The number of cases drops to 500. He/she then adds hypertension as a comorbid condition. The case number drops to 100. If they add the symptom "shortness of breath," the case number drops to 11. This may not be an optimal number of cases for a credible study or analysis. Therefore, the user can immediately go back and change criteria to increase the patient case yield.

For certain search sections (conditions and procedures), a user enter the system by using relevant diagnostic or procedure codes in addition to entering and searching via free text. In some examples, when a user starts typing text for diagnoses or procedures, a list of codes that have description matching the text are shown as suggestions. The user can continue typing their desired text to perform free text search, or they can pick one of the recommended codes to perform a search for that specific code. In this example, both the codes and the user-entered text represent potential indications of a clinical condition.

Figure 8:
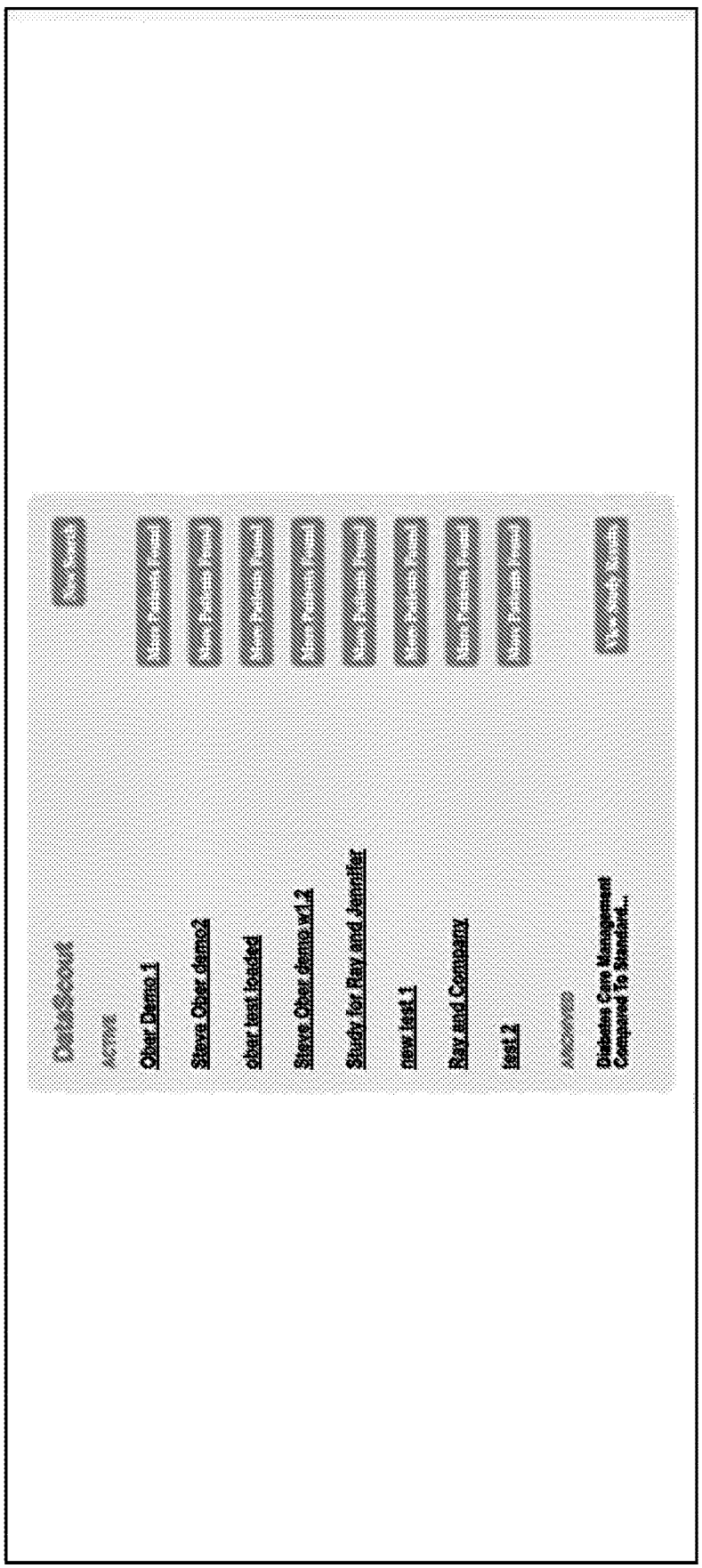

When first accessing the computer system via the user interface, a user may be presented with a "dashboard" screen as shown in FIG. 8. This dashboard allows the user to easily begin a new search or continue with one previously performed. The name of each search is on the left side of the screen. In some examples, a user may have an ability to delete of prior searches by moving those searches to a trashcan. The trash may have a holding period of few days, after which a prior search may be completely removed. In other examples, users may have an ability to clone an existing search to use as a starting point. This would allow users to avoid entering all specified clinical conditions from scratch when a new search is similar to a prior search.

Following a user selection of the "new search" tab on the dashboard screen, the user may be presented with the screen as shown in FIG. 9. The user selects a name for a new study. The number of eligible patients in the database is listed on the upper right of the page. The user now begins to select the main clinical condition on which to search.

Figure 10:
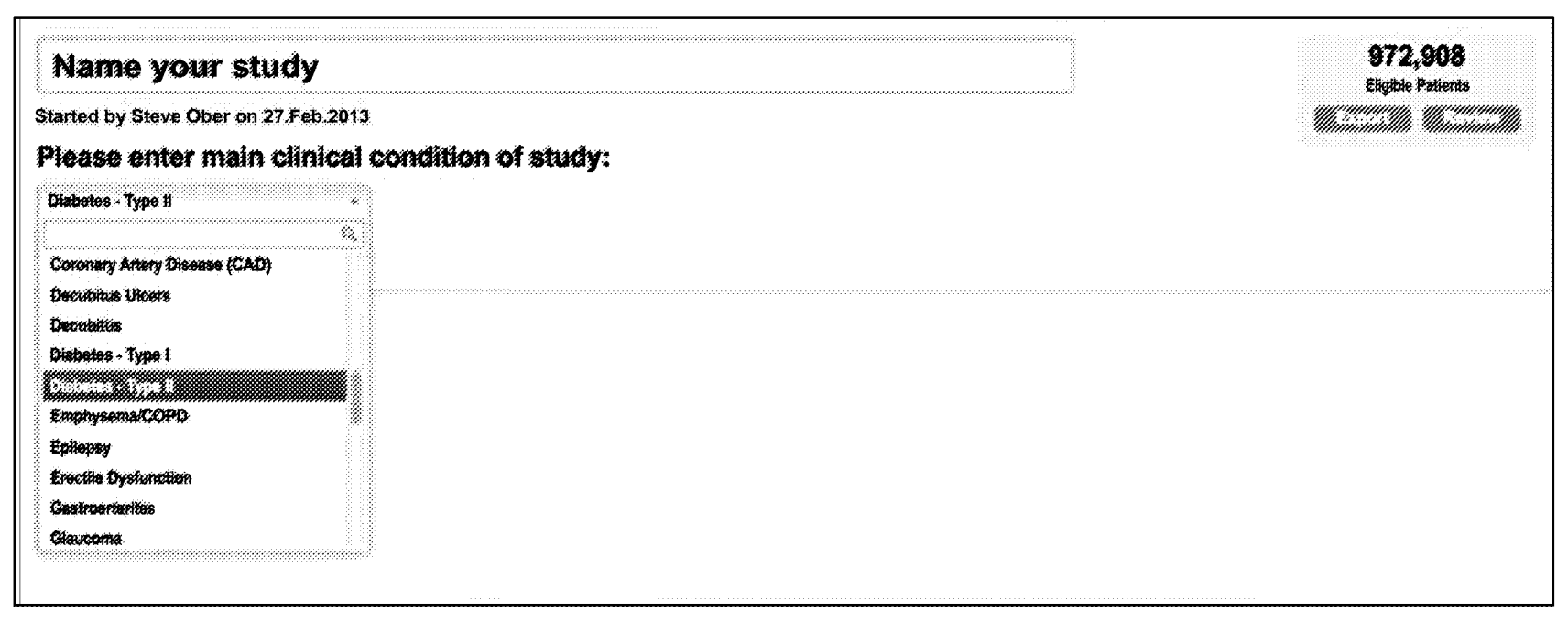

As shown in FIG. 10, the user can manually type in a disease state or select one from the drop down menu. In the example of FIG. 10, the user selected Diabetes Type II from the drop down menu.

Figure 11:
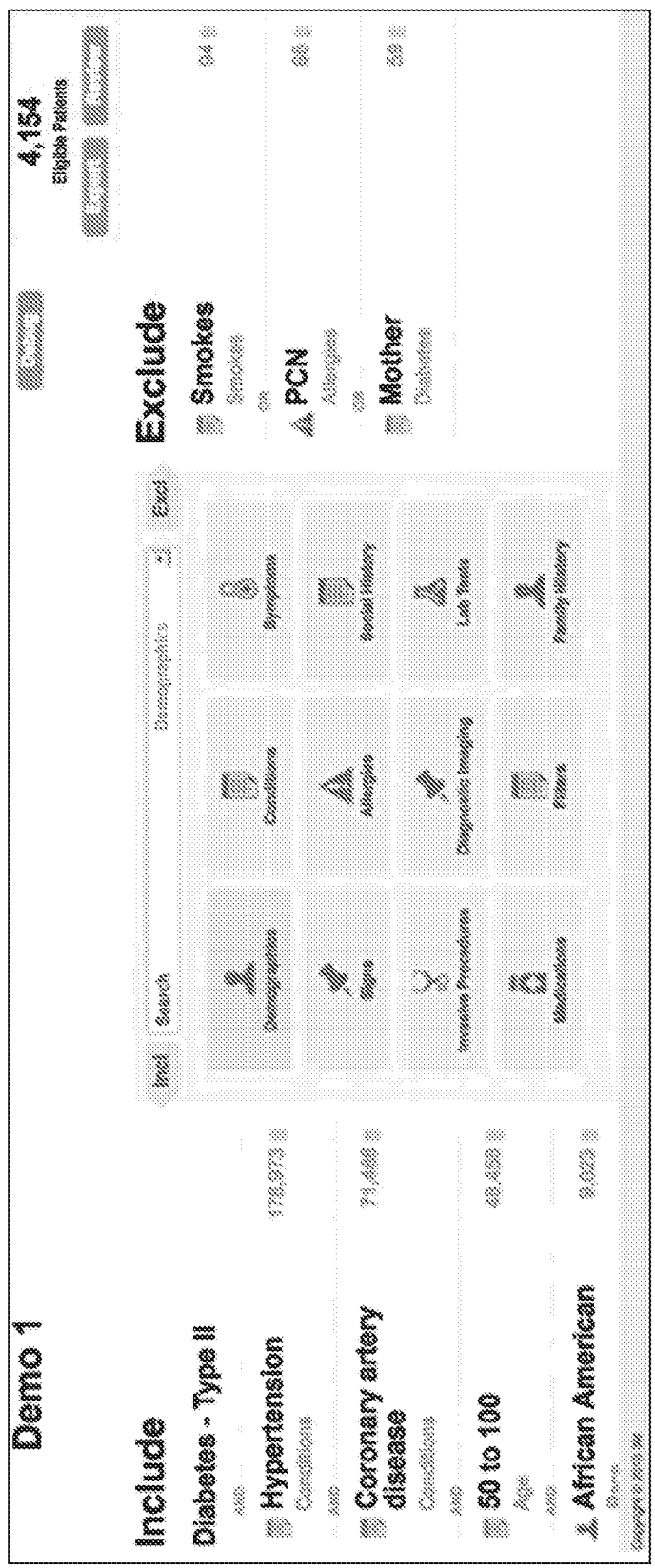

As shown in FIG. 11, the user may then begin to select patient criteria guided by the twelve icons in the middle of the screen. Each icon has criteria that may drop down for the user to select, or the user can type in a key term in the search bar above the icons at any time. Once a criteria is selected, the user can "include" or "exclude" it from the overall patient criteria list. In the screen of FIG. 11, the user wants to find Type II Diabetic patients who also have hypertension, coronary artery disease, are age 50-70 and are African American. However, the user wants to "exclude" patients who smoke, have an allergy to penicillin and whose mothers had diabetes. Each selected criteria is listed to the left (include) or right (exclude) sections if the screen. The small numbers to the right of each selected criteria are the number of patients that met that criteria. In the screen below, there were 94 patients excluded from selection because they smoked. There were 71,488 patients that were included and had coronary artery disease. The box in the upper right of the screen keeps a running tally of the total number of patients that have currently been selected based on all the criteria having been selected up to that point in the analysis.

Figure 12:
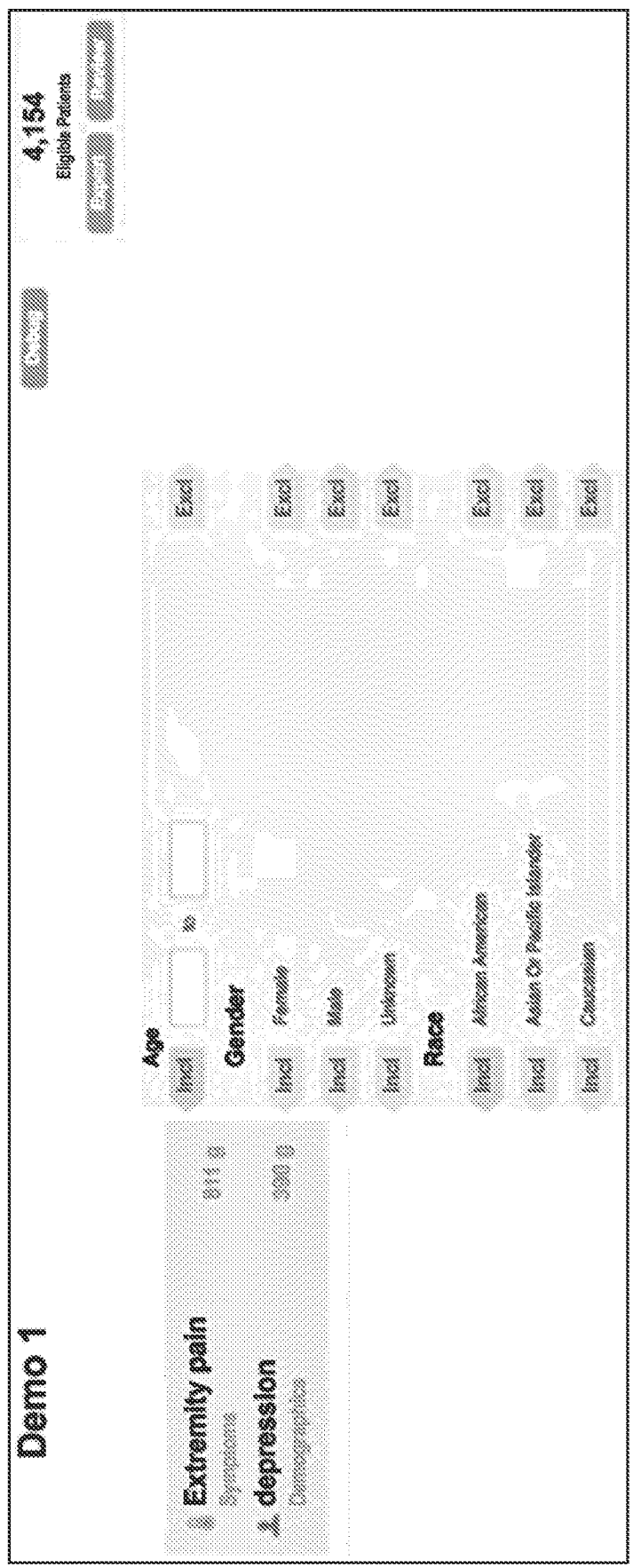

The screen of FIG. 12 illustrates a drop down menu that is presented following a user selection of the demographics icon. All screens scroll up and down to show all the choices on a screen. In some examples, the user interface may provide guidance using type-aheads and suggestions to fill in a user's query. In some examples, the computer system may recognize the clinical domain in which a user is working and autocorrect with a limited set of terms related to that domain. For example, if a user working in the area of "Diabetes" and is trying to type "insulin" . . . The system may offer up the following terms after typing "ins" . . . : Insulin, insulin dependent, synthetic insulin. Understanding the context of the user's query, the computer system may not offer up insulated, insurance, which are presumed to be irrelevant terms within the clinical domain. In this manner, the computer system may higher preference to context of clinical domain, followed by low relevance terms. In this manner, user searches are facilitated without being restrictive in what can be searched for. In addition, the deviations from the presented recommendations would be used as feedback for improving the relevance of further suggestions.

Figure 13:
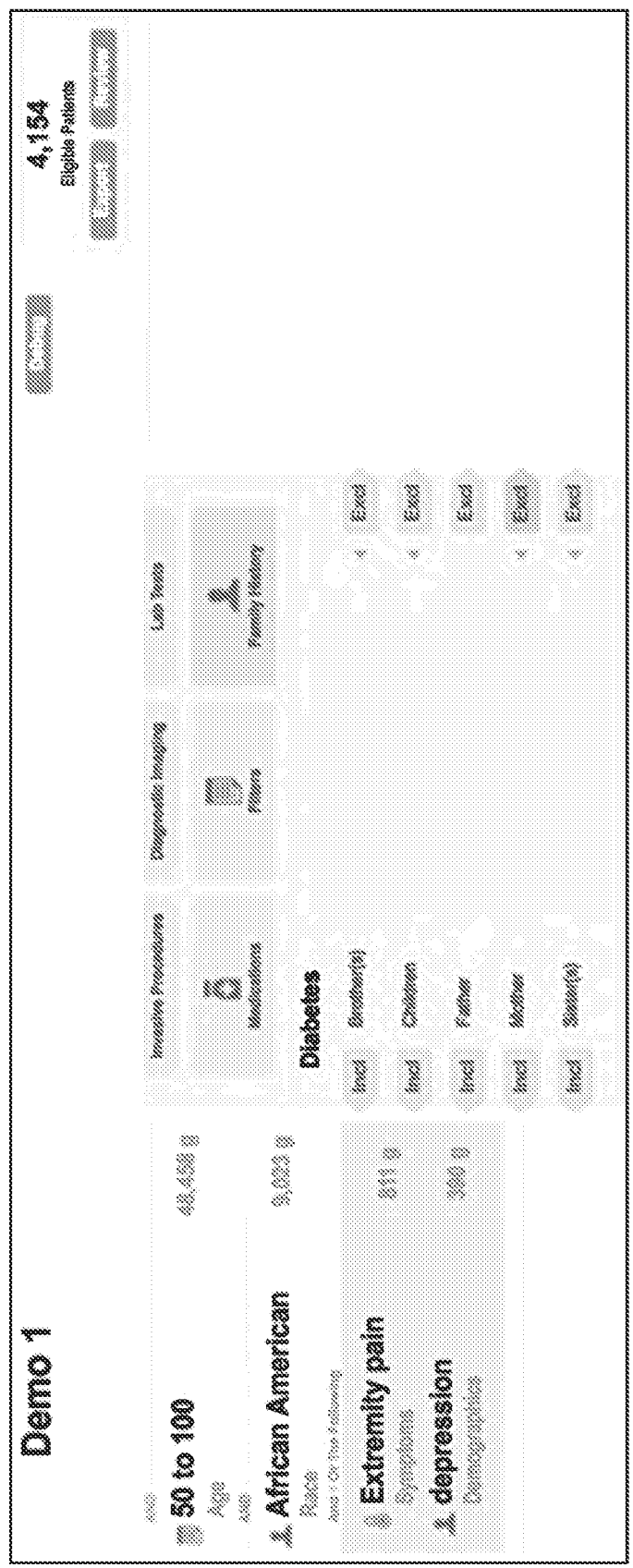

The screen of FIG. 13 illustrates a drop down menu that is presented following a user selection of the family history icon. On the screen, the user selected "mother" and Excl (exclude). The result of that selection appears on the right side of the screen higher up on the page (see FIG. 11). Note that on the left part of the screen the user selected "extremity pain" or "depression" in their list of inclusion criteria. Up to this point all the selected criteria used "and" logic. "And" is the default logic for selected inclusion criteria. However, by clicking on the word "and" the user can change this logic to "or" logic. Now the user is telling the computer system to include patients who have extremity pain or depression.

Figure 14:
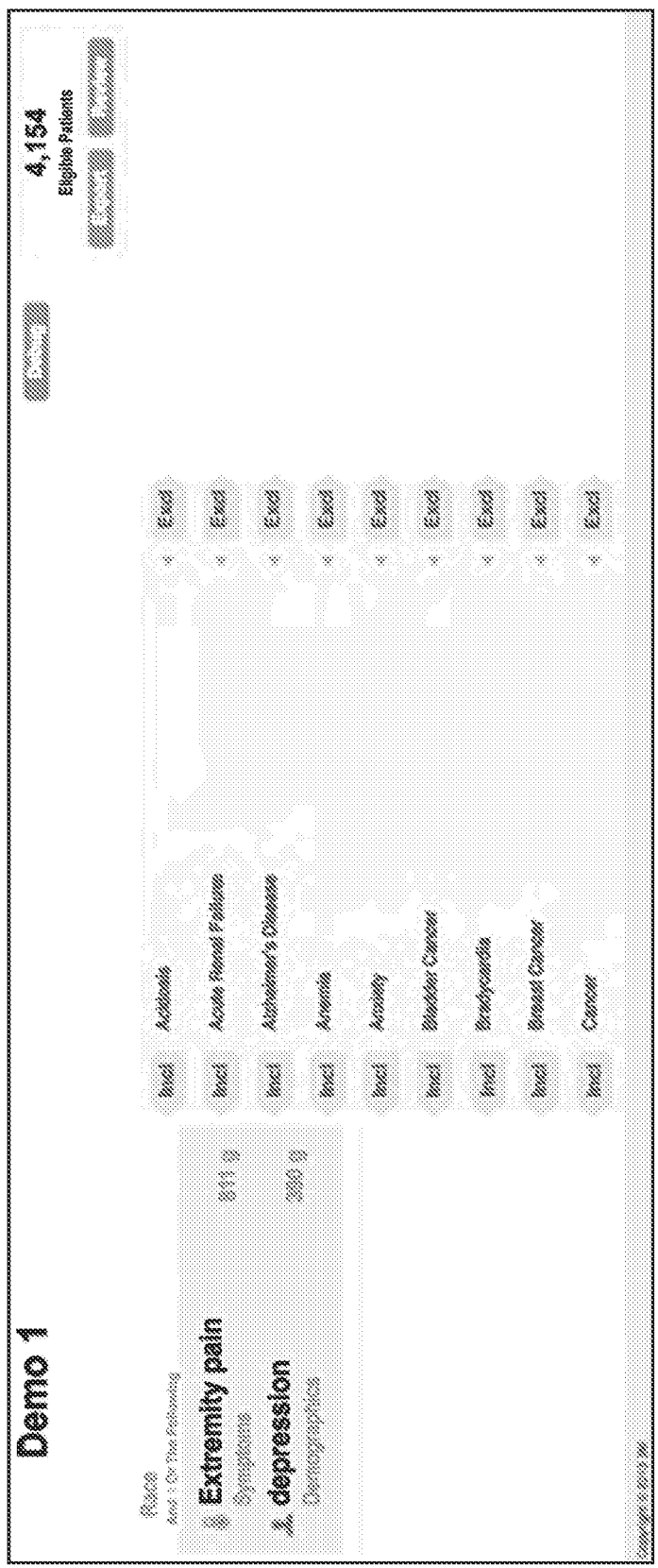

The screen of FIG. 14 illustrates a drop down menu that is presented following a user selection of the conditions icon.

Figure 15:
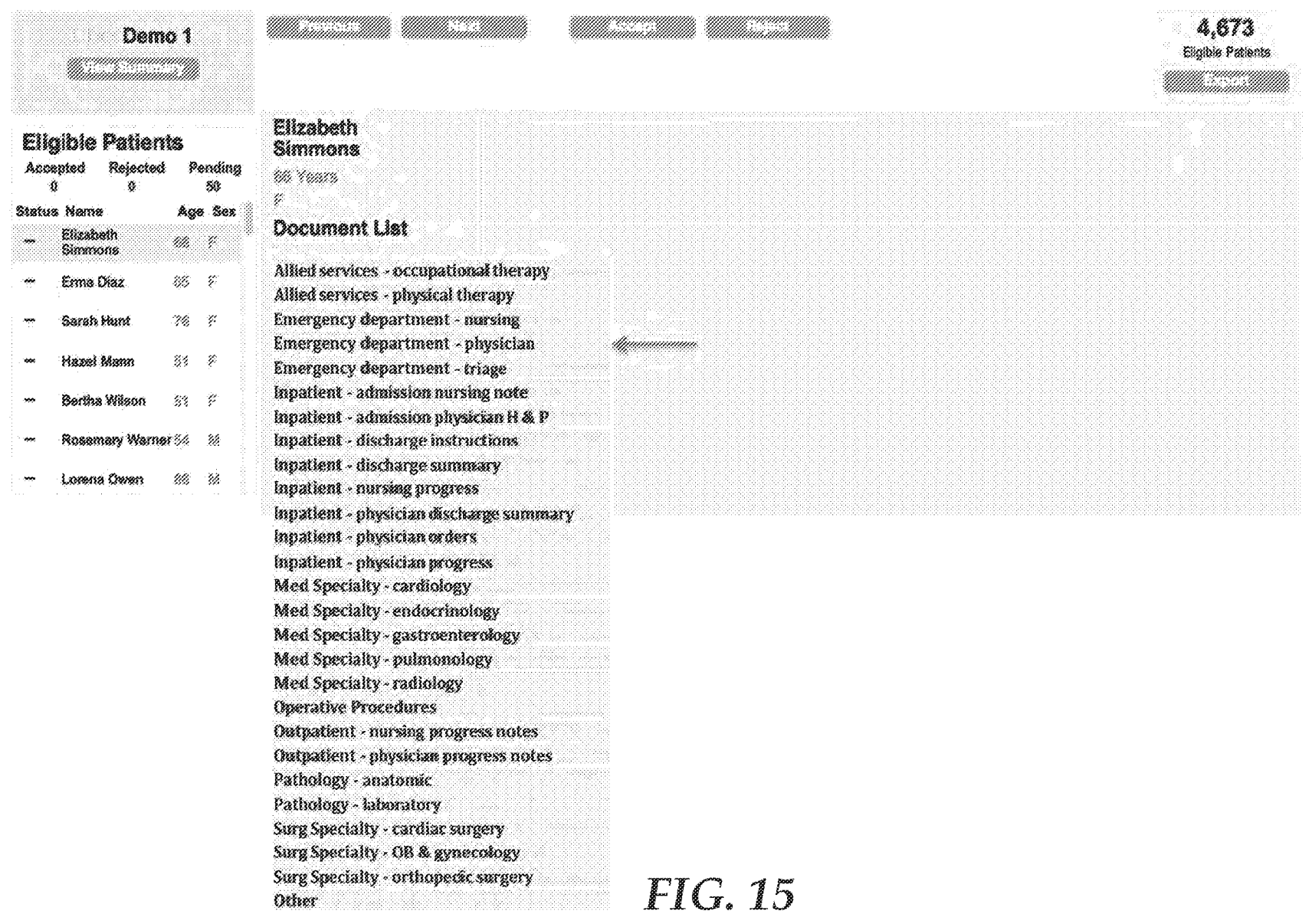

The screen of FIG. 15 is presented following a user selection of the "review" button on the top right of the screen. This screen documents of all the patients selected are reviewed by the user. The list of patients selected appears at the far left of the screen. In the screen below, the user wants to see the document from the emergency department dictated by the physician (blue arrow) for the first subject on the list (Elizabeth Simmons).

Figure 16:
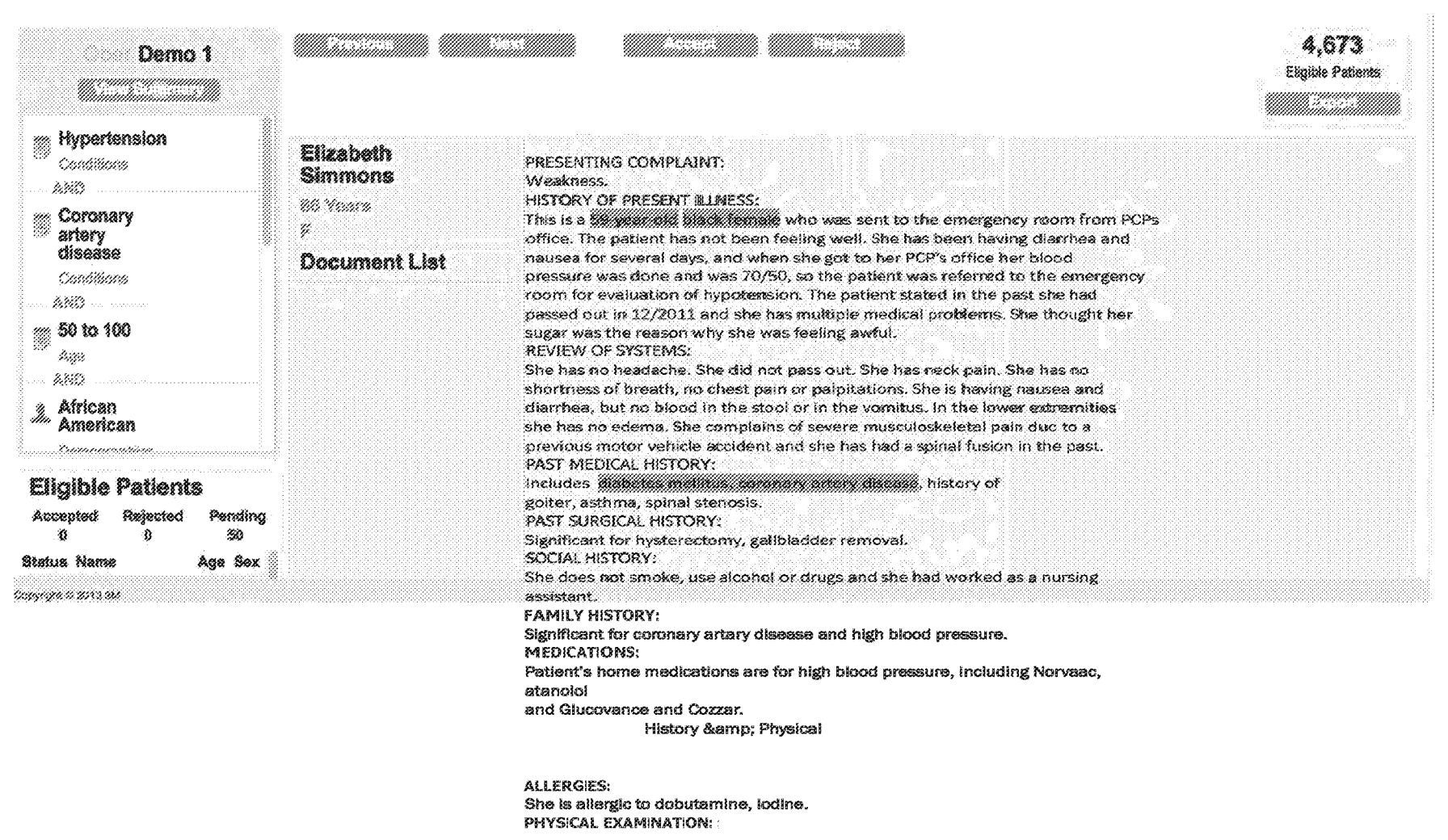

The screen of FIG. 16 is presented following a user selection of the document type associated with the selected subject. As shown on FIG. 16, the actual document is presented to allow the user to review the Indications of the selected clinical condition criteria are highlighted in the document. On the left, the user can view a summary of all the criteria selected (hypertension, coronary artery disease, etc.).

In this manner, once a search is complete, a user can pull up each case found and review it for accuracy and appropriateness for study enrollment. These cases can be stored and called up in the future as needed for further review. The user may navigate through the list, and review the result-set. In some examples, each identified subject in the result-set may start out in a Pending Review state. The user can either Approve those, Reject those, or leave them in Pending Review state. In addition, at any time during the review process, user can go back and modify their search criteria. The eligible patient list would be updated accordingly.

The users can browse through the list of eligible cases. This list contains basic patient information, along with a case level review status. In addition, there is a summary of Review progress showing counts for how many cases have been approved, rejected, and are still pending.

The techniques described in this disclosure may be implemented, at least in part, in hardware, software, firmware, or any combination thereof. For example, various aspects of the described techniques may be implemented in a wide variety of computer devices, such as servers, laptop computers, desktop computers, notebook computers, tablet computers, hand-held computers, smart phones, and the like. Any components, modules or units have been described provided to emphasize functional aspects and does not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

Within such examples and others, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

The techniques described in this disclosure may also be embodied or encoded in a computer system-readable medium, such as a computer system-readable storage medium, containing instructions. Instructions embedded or encoded in a computer system-readable medium, including a computer system-readable storage medium, may cause one or more programmable processors, or other processors, to implement one or more of the techniques described herein, such as when instructions included or encoded in the computer system-readable medium are executed by the one or more processors. Computer system readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer system readable media. In some examples, an article of manufacture may comprise one or more computer system-readable storage media.

Various examples have been described. These and other examples are within the scope of the following claims.

What is claimed is:

1. A method of classifying a plurality of subjects associated with medical documents, the method comprising:

presenting, via a user interface of a computer system, a dashboard screen;

receiving, via the dashboard screen of a computer system, an indication of at least one clinical concept;

upon receiving the indication of the at least one clinical concept, using a natural language processing (NLP) engine with the computer system to prioritize one or more locations in each one of the medical documents to search for the at least one clinical concept, wherein the prioritization is determined based on at least identifying one or more relevant fields to search in each of the medical documents based on one or more medical conditions for which a subject associated with the clinical concept is medically evaluated;

upon prioritizing the plurality of sections based on associations of the sections to the at least one clinical concept, parsing, with the computer system, the medical documents for corresponding indications of the at least one clinical concept, the corresponding indications are located within at least one section of a prioritized plurality of sections;

identifying, with the computer system using the NLP engine, subjects in the plurality of subjects as meeting the at least one clinical concept based at least in part on the prioritization of sections within the medical documents and locations of the corresponding indications of the at least one clinical concept within the medical documents and whether the one or more subjects in the plurality of subjects are associated with medical documents that include indications that correlate to the indication of the at least one clinical concept received by the computer system, wherein the indications that correlate to the indication of the at least one clinical concept received by the computer system include ontologies of the indication of the at least one clinical concept received by the computer system and identifying the ontologies of the indication of the at least one clinical concept received by the computer system comprises:

statistically analyzing the distribution, incidence and prevalence of terms within the medical documents that include indications of the at least one clinical concept matching the indication of the at least one clinical concept received by the computer system;

comparing the distribution, incidence and prevalence of the terms within the medical documents that include indications of the at least one clinical concept matching the indication of the at least one clinical concept received by the computer system with the distribution, incidence and prevalence of the same terms within all the medical documents to find terms correlated with the indications of the at least one clinical concept; and identifying the terms that correlate to the indications of the at least one clinical concept in the medical documents that include indications of the at least one clinical concept matching the indication of the at least one clinical concept received by the computer system as ontologies of the indication of the at least one clinical concept; and outputting, to the dashboard screen in real time, indications of the subjects in the plurality of subjects identified as meeting the at least one clinical concept.

2. The method of claim 1, wherein the sections represent predefined sections of common encounter documents.

3. The method of claim 1, wherein the indication of the at least one clinical concept is associated with sections having higher priority within the prioritization of sections.

4. The method of claim 1, further comprising accessing, with the computer system, a database identifying ontologies of the indication of the at least one clinical concept received by the computer system.

5. The method of claim 1, further comprising identifying ontologies of the indication of the at least one clinical concept received by the computer system by analyzing, with the computer system, the medical documents that include indications of the at least one clinical concept matching the indication of the at least one clinical concept received by the computer system.

6. The method of claim 1, further comprising identifying ontologies of the indication of the at least one clinical concept received by the computer system by running the NLP engine, with the computer system, to search the medical documents that include indications of the at least one clinical concept matching the indication of the at least one clinical concept received by the computer system for textual similarities.

7. The method of claim 1, wherein the indications that correlate to the indication of the at least one clinical concept received by the computer system include quantitative indications of the at least one clinical concept.

8. The method of claim 7, further comprising accessing, with the computer system, a database identifying the quantitative indications of the at least one clinical concept.

9. The method of claim 7, further comprising identifying the quantitative indications of the at least one clinical concept by analyzing, with the computer system, the medical documents that include indications of the at least one clinical concept matching the indication of the at least one clinical concept received by the computer system.

10. The method of claim 7, further comprising identifying the quantitative indications of the at least one clinical concept, with the computer system, by searching the medical documents that include indications of the at least one clinical concept matching the indication of the at least one clinical concept received by the computer system for quantitative similarities.

11. The method of claim 7, further comprising identifying the quantitative indications of the at least one clinical concept by:

statistically analyzing the distribution, incidence and prevalence of quantitative factors within the medical documents that include indications of the at least one clinical concept matching the indication of the at least one clinical concept received by the computer system;

comparing the distribution, incidence and prevalence of the quantitative factors within the medical documents that include indications of the at least one clinical concept matching the indication of the at least one clinical concept received by the computer system with the distribution, incidence and prevalence of the same quantitative factors within all the medical documents to find quantitative factors correlated with the indications of the at least one clinical concept; and identifying the quantitative factors that correlate to the indications of the at least one clinical concept as the quantitative indications of the at least one clinical concept.

12. The method of claim 1, further comprising indexing data parsed from the medical documents.

13. The method of claim 1, wherein the at least one clinical concept includes one or more of a group consisting of:
a chief complaint of the subject;
a history of present illness of the subject;
a past medical history of the subject;
a social history of the subject;
a family history of the subject;
a review of systems of the subject;
allergies of the subject;
medications of the subject;
impressions of the subject by a clinician;
a medical plan for the subject;
diagnostic imaging results preformed the subject;
results of a medical test of the subject;
a gender of the subject;
an ethnicity of the subject;
an age of the subject;
a physical attribute of the subject;
physical signs of the subject; and
physical systems of the subject.

14. The method of claim 1, further comprising acquiring the medical documents with the computer system.

15. The method of claim 1, further comprising accessing the medical documents with the computer system from a database.

16. The method of claim 1, wherein the medical documents comprise one or more of:
government-acquired medical documents from a Medicare repository;
medical documents submitted to a government by the medical facility;
medical documents submitted to the government by many medical facilities;
medical documents received from one or more medical facilities;
medical documents received from one or more insurance companies; and
medical documents associated with all-payer health insurance claims.

17. The method of claim 1, wherein the medical documents comprise one or more of:
medical clinician notes;
medical clinician dictations;
medication files;
radiology reports;
emergency department; and
subject pathology reports.

18. The method of claim 1, further comprising sending the indications of the subjects in the plurality of subjects identified as meeting the at least one clinical concept from the computer system to a client computer, wherein the client computer presents the indications of the subjects in the plurality of subjects identified as meeting the at least one clinical concept to a user.

19. The method of claim 18, wherein the computer system sends the indications of the subjects in the plurality of subjects identified as meeting the at least one clinical concept to the client computer via an internet protocol (IP).

20. The method of claim 1, further comprising selecting one or more sections having higher priority within the prioritization of sections instead of other sections having lower priority within the prioritization of sections, wherein identifying subjects in the plurality of subjects as meeting the at least one clinical concept comprises identifying subjects in the plurality of subjects as having the one or more sections having higher priority being associated with the at least one clinical concept.

21. The method of claim 1, wherein outputting indications of the subjects in the plurality of subjects identified as meeting the at least one clinical concept occurs even if the indication of the clinical concept is not specifically mentioned in the medical documents.

22. The method of claim 1, wherein the NLP engine allows analysis of data from the medical document having both unstructured and structured components.

23. The method of claim 1, wherein the prioritization of the plurality of sections within the medical document is based on the type of clinical concept received.

24. The method of claim 23, wherein data in a first section conflicts with data in a second section from the plurality of sections for the same patient.

25. The method of claim 1, wherein the NLP engine directs a user to a section based on whether the clinical concept is a diagnosis, sign, or symptom.

* * * * *